(12) United States Patent
Pulugurtha (10) Patent No.: US 9,943,628 B2
(45) Date of Patent: Apr. 17, 2018

(54) WELDED STENT WITH RADIOPAQUE MATERIAL LOCALIZED AT THE WELDS AND METHODS

(71) Applicant: Medtronic Vascular, Inc., Santa Rosa, CA (US)

(72) Inventor: Syamala Rani Pulugurtha, Santa Rosa, CA (US)

(73) Assignee: Medtronic Vascular Inc., Santa Rosa, CA (US)

( * ) Notice: Subject to any disclaimer, the term of this patent is extended or adjusted under 35 U.S.C. 154(b) by 149 days.

(21) Appl. No.: 14/447,286

(22) Filed: Jul. 30, 2014

(65) Prior Publication Data

US 2016/0030644 A1 Feb. 4, 2016

(51) Int. Cl.
| | | |
|---|---|---|
| *A61F 2/82* | (2013.01) | |
| *A61L 31/18* | (2006.01) | |
| *A61L 31/02* | (2006.01) | |
| *B23K 26/20* | (2014.01) | |
| *A61F 2/915* | (2013.01) | |

(52) U.S. Cl.
CPC .............. *A61L 31/18* (2013.01); *A61F 2/82* (2013.01); *A61F 2/915* (2013.01); *A61L 31/022* (2013.01); *B23K 26/20* (2013.01); *A61F 2250/0032* (2013.01); *A61F 2250/0098* (2013.01)

(58) Field of Classification Search
None
See application file for complete search history.

(56) References Cited

U.S. PATENT DOCUMENTS

| | | | |
|---|---|---|---|
| 4,213,026 A | 7/1980 | Duvall | |
| 5,817,152 A | 10/1998 | Birdsall | |
| 6,136,023 A | 10/2000 | Boyle | |
| 6,174,329 B1 * | 1/2001 | Callol | A61F 2/90 606/194 |
| 6,692,522 B1 | 2/2004 | Richter | |
| 2003/0225448 A1 * | 12/2003 | Gerberding | A61F 2/91 623/1.15 |
| 2006/0237407 A1 | 10/2006 | Nguyen et al. | |
| 2007/0112415 A1 * | 5/2007 | Bartlett | A61F 2/90 623/1.15 |
| 2008/0234795 A1 * | 9/2008 | Snow | A61F 2/91 623/1.11 |
| 2008/0319530 A1 * | 12/2008 | Leewood | A61F 2/07 623/1.16 |
| 2009/0005853 A1 * | 1/2009 | Osman | A61F 2/915 623/1.15 |
| 2011/0009941 A1 * | 1/2011 | Grandfield | A61F 2/91 623/1.11 |

(Continued)

FOREIGN PATENT DOCUMENTS

WO WO2009/030748 3/2009

OTHER PUBLICATIONS

Carpenter Technology Corp. Tech, Datasheet for MP35N, edition date: Aug. 1, 2012.

(Continued)

*Primary Examiner* — Thomas J Sweet
*Assistant Examiner* — Megan Wolf (57) ABSTRACT

A stent that includes a stent body and one or more weld joints, wherein the weld joints include a radiopaque material, and a method of making a stent that includes using a radiopaque filler material in a welding process.

23 Claims, 4 Drawing Sheets

(56) References Cited

U.S. PATENT DOCUMENTS

| | | |
|---|---|---|
| 2011/0147080 A1* | 6/2011 | Slininger ............... H01R 4/625 |
| | | 174/84 R |
| 2011/0224771 A1 | 9/2011 | Schwager |
| 2012/0067454 A1* | 3/2012 | Melder ................... A61F 2/915 |
| | | 141/2 |
| 2013/0197627 A1 | 8/2013 | Jensen et al. |
| 2014/0014530 A1 | 1/2014 | Lin |

OTHER PUBLICATIONS

ASM Specialty Handbook: Nickel, Cobalt, and Their Alloys, Joseph R. Davis, editor, pp. 401-406: Fabrication and Metallography of Cobalt Alloys (2000 ASM International).

Medical Device Materials: Proceedings of the Materials & Processes for Medical Devices Conference, Sanjay Shrivastava, editor, pp. 31-36: Peculiarities of Micro Laser Welding of Medical Devices (2004 ASM International).

PCT/US2015/039166, The International Search Report and the Written Opinion of the International Searching Authority, dated Sep. 11, 2015.

\* cited by examiner

WELDED STENT WITH RADIOPAQUE MATERIAL LOCALIZED AT THE WELDS AND METHODS

BACKGROUND

Conventionally, a medical stent (hereinafter also abbreviated as 'stent') is placed to a stricture in a lumen inside a living body such as a blood vessel, a digestive tract, a bile duct, a pancreatic duct, or a urinary duct, for example, in order to expand this stricture and/or maintain an open state. Stents are generally thin walled tubular-shaped devices composed of complex patterns of interconnecting struts which function to hold open a segment of such lumens. Commercially available stents are typically implanted by use of a catheter which is inserted at an easily accessible location and then advanced through the vasculature to the deployment site. A stent is initially maintained in a radially compressed or collapsed state to enable it to be maneuvered through the lumen. Once in position, the stent is deployed into a radially-expanded configuration. In the case of a self-expanding stent, deployment is achieved by the removal of a constraint, such as the retraction of a delivery sheath. In the case of a balloon expandable stent, deployment is achieved by inflation of a dilation balloon about which the stent is carried on a stent-delivery catheter.

A stent should have adequate radial strength (i.e., hoop strength) to withstand structural loads, particularly radial compressive forces imposed on the stent as it supports the walls of a vessel lumen, even in the event of vessel spasm, and it should be longitudinally flexible to allow it to be maneuvered through a tortuous path and to enable it to conform to a site that may not be strictly linear or may be subject to flexure. The material from which a stent is constructed should allow the stent to undergo radial expansion which typically requires substantial deformation of localized portions of the stent's structure. Once expanded, a stent should maintain its size and shape throughout its service life. Also, the material of which the stent is made should be biocompatible so as not to trigger any adverse vascular responses.

In addition to these requirements, a stent should also be viewable under radioscopy. This is because the position of the stent needs to be confirmed by fluoroscopy or fixed X-ray equipment while placing the stent into position, after it is positioned, as well as during removal, if necessary. Thus, a stent should also be radiopaque to allow for real time visualization. That is, a stent or components thereof should block or attenuate the passage of X-rays more than the surrounding tissue.

This is typically accomplished by the use of radiopaque materials in the construction of a stent, which allows for its direct visualization. The most common materials used to fabricate stents are stainless steel and nickel-titanium alloys, neither of which is particularly radiopaque. This factor, in combination with the relatively thin wall thickness (about 0.002 to 0.006 inch) of most stent designs renders stents produced from these materials insufficiently radiopaque to be adequately visualized with fluoroscopy procedures. Alternatively, high density biocompatible metals, such as tantalum, iridium, platinum, gold, and the like, may lack suitable physical properties, e.g. flexibility, elasticity, tensile strength, may be too costly, and may be excessively radiopaque. Also, stents constructed of only highly radiopaque materials may appear overly bright when viewed under a fluoroscope, thereby obscuring visualization of the stented lumen. Thus, stents have been designed that combine different materials to produce a mechanically sound, biocompatible, and fluoroscopically visible stent.

One approach that has been used to increase the radiopacity of stents is through attaching radiopaque markers to the stent. Using such markers of sufficient size and quantity distributed over the body of the stent can provide a pixelated or compound image that informs the clinician of the location, orientation, and shape, e.g. degree of deployment of the stent in the patient. Radiopaque markers, however, may project from the surface of the stent. If the markers project inwardly, fluid flow may be disrupted. If they project outwardly, the wall of the lumen wall tissue may be damaged. In an alternative approach, the radiopacity of stents has also been increased by plating or coating selected portions thereof with radiopaque material. However, under certain conditions cracks may form in the plating or coating causing portions of the plating to separate from the underlying substrate. This has the potential for creating jagged edges that may inflict physical trauma on the lumen wall tissue or cause turbulence in the blood flowing past the stent, thereby inducing thrombogenesis. Thus, composite stents, whether equipped with markers or radiopaque plating, have several disadvantages; namely, separation of the markers, plating, or coating from the substrate material, which may allow the metallic particles to flow downstream within a vessel lumen causing potential blockages or other adverse effects upon the patient. One approach to overcome these shortcomings of composite devices is a stent formed from a single material that possesses the required mechanical and radiopaque properties. An example of such a material is a binary alloy of either tantalum-tungsten or tantalum-niobium; however, the cost and complexity of manufacture of such devices is undesirable.

SUMMARY

The present disclosure provides a stent that includes a stent body and one or more weld joints, wherein the weld joints include a radiopaque material. More specifically, the radiopaque material is localized at the weld joints (relative to the stent body).

This stent construction is made by a method that includes using a radiopaque filler material in a welding process. More specifically, a method of the present disclosure provides a method of making a stent: providing a stent having a stent body with one or more struts constructed of a stent body material; providing a radiopaque filler material that is different from the stent body material; and welding the stent body at a junction between the one or more struts with the radiopaque filler material to form one or more weld joints comprising the radiopaque material.

Herein, the following definitions are used:

A "weld joint" or "welding joint" is the portion or portions of a stent (e.g., point or edge) where two or more portions of a stent body are joined together to form a bond that includes material from the stent body and a radiopaque filler material. The joints are formed by welding two or more portions of a stent body together with a radiopaque filler material. Thus, a weld joint is includes a solid mixture of material from the radiopaque filler and stent body.

A "stent body" is all portions of the stent that are not directly within a weld joint.

The phrase "localized at" in the context of the location of the radiopaque material means that the radiopaque material is at a higher concentration at the weld than in the stent body.

Radiopaque materials are those that inhibit the passage of electromagnetic radiation, particularly X-rays. Using analog X-ray film, such materials have a whiter appearance compared with a relatively dark appearance of more radiolucent materials. Digital X-ray images usually appear inverted such that radiopaque components appear dark gray or black. To determine whether a particular medical device component, e.g., a stent weld, may be sufficiently radiopaque for the intended implant location in a human patient, a designer may utilize ASTM F640-12 "Standard Test Methods for Determining Radiopacity for Medical Use."

The terms "comprises" and variations thereof do not have a limiting meaning where these terms appear in the description and claims. Such terms will be understood to imply the inclusion of a stated step or element or group of steps or elements but not the exclusion of any other step or element or group of steps or elements. By "consisting of" is meant including, and limited to, whatever follows the phrase "consisting of." Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and may or may not be present depending upon whether or not they materially affect the activity or action of the listed elements.

The terms "preferred" and "preferably" refer to claims of the disclosure that may afford certain benefits, under certain circumstances. However, other claims may also be preferred, under the same or other circumstances. Furthermore, the recitation of one or more preferred claims does not imply that other claims are not useful, and is not intended to exclude other claims from the scope of the disclosure.

The terms such as "a," "an," and "the" are not intended to refer to only a singular entity, but include the general class of which a specific example may be used for illustration. The terms "a," "an," and "the" are used interchangeably with the term "at least one." The phrases "at least one of" and "comprises at least one of" followed by a list refers to any one of the items in the list and any combination of two or more items in the list.

The term "or" is generally employed in its usual sense including "and/or" unless the content clearly dictates otherwise. The term "and/or" means one or all of the listed elements or a combination of any two or more of the listed elements.

Also herein, all numbers are assumed to be modified by the term "about" and in certain embodiments by the term "exactly." As used herein in connection with a measured quantity, the term "about" refers to that variation in the measured quantity as would be expected by the skilled artisan making the measurement and exercising a level of care commensurate with the objective of the measurement and the precision of the measuring equipment used.

The recitations of numerical ranges by endpoints include all numbers subsumed within that range as well as the endpoints (e.g., 1 to 5 includes 1, 1.5, 2, 2.75, 3, 3.80, 4, 5, etc.).

The above summary of the present disclosure is not intended to describe each disclosed embodiment or every implementation of the present disclosure. The description that follows more particularly exemplifies illustrative embodiments. In several places throughout the application, guidance is provided through lists of examples, which examples may be used in various combinations. In each instance, the recited list serves only as a representative group and should not be interpreted as an exclusive list.

DESCRIPTION OF EXEMPLARY EMBODIMENTS

The present disclosure provides a stent that includes a stent body and one or more weld joints, wherein the weld joints (i.e., welding joints) include a radiopaque material.

More specifically, the radiopaque material is localized at the weld joints (relative to the stent body). Such stent constructions can be made by a method that includes using a radiopaque filler material (e.g., filler wire) in a welding process (e.g., laser welding, spot welding, resistance welding, MIG welding) to form a weld between struts (e.g., at the crown portions) of a stent. As a result of the radiopaque material localized in the weld joints, not only is the stent more visible under fluoroscopy as well as magnetic resonance imaging (MRI), it is less costly to manufacture.

Figure 1A:
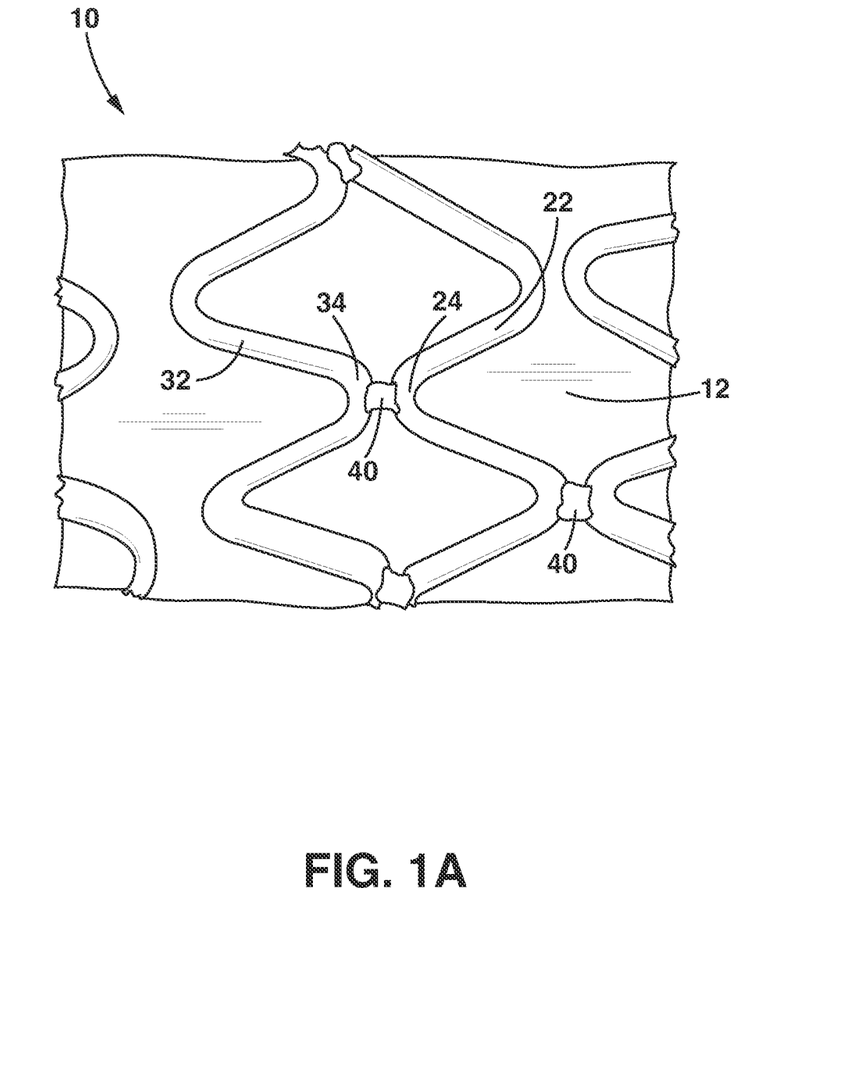
FIG. 1A depicts one exemplary embodiment of a portion of a stent including a weld joint connecting adjacent struts.
Figure 1B:
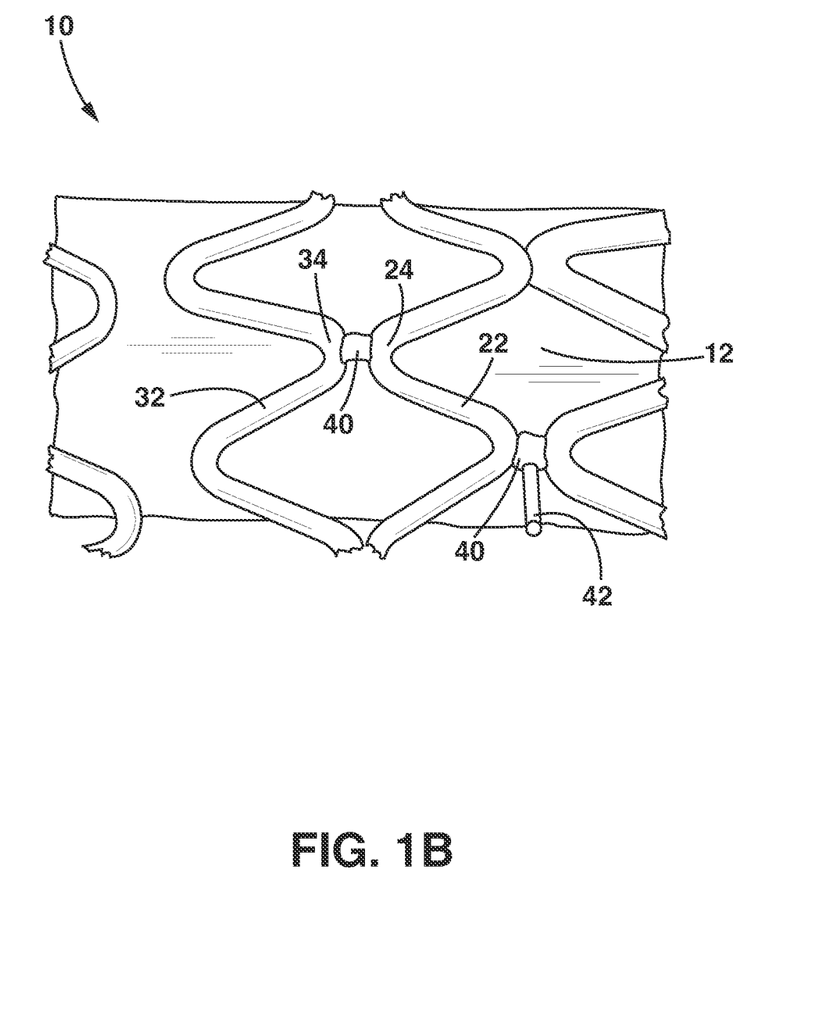
FIG. 1B is a view of the weld joint depicted in FIG. 1A before removal of excess filler wire extending from the weld joint.

A portion of one exemplary embodiment of a stent having a stent body 10 located on a support surface 12 (e.g., a mandrel, etc.) is shown in FIGS. 1A and 1B. The exemplary embodiment of the stent depicted in FIG. 1A has a stent body 10 constructed of struts, including a pair of struts 22 and 32, each of which includes a crown portion 24 and 34, respectively. In the depicted embodiment, adjacent crown portions 24 and 34 of stent 10 are connected to each other through a weld joint 40 located between crown portions 24 and 34 of struts 22 and 32.

As depicted in FIG. 1B, excess filler wire 42 is shown still attached to the weld joint 40. This excess filler wire 42 can be mechanically cut or laser cut, for example, after the weld joint 40 is formed.

Although one exemplary embodiment of a stent is shown in FIGS. 1A and 1B, stents including weld joints as described in the present disclosure may include a wide variety of configurations that may include one or more weld joints. For example, although the depicted exemplary embodiment of a stent includes a weld joint located between adjacent crown portions of adjacent struts, the weld joints found in stents as described herein may be located between struts or between any other features at other locations with the structure of the stent. In one or more embodiments, stents are composed of an intricate geometric pattern of interconnecting elements (e.g., cylindrical rings and connecting links) commonly referred to as struts. In certain embodiments, a stent of the disclosure may be formed from a tube by laser cutting a pattern of cylindrical rings and connecting links in the tube, e.g. U.S. Pat. No. 6,131,266 to Saunders. Connections between elements in such laser-cut stents are typically designed into the cut pattern such that no secondary joining steps are required. However, the cut pattern can be modified, e.g. by making cuts where some connections were previously left intact, such that the radiopaque weld connections of this invention can be additionally used in laser-cut stents in order to enhance radiopacity.

Alternatively, a stent may be formed by laser cutting a pattern in a flat metal sheet, and then rolling the pattern into the shape of the cylindrical stent to form the desired rings and links and providing a longitudinal weld to form the stent, e.g. U.S. Pat. No. 6,692,522 to Richter. Other methods of forming stents are well known and include chemically etching a flat metal sheet and rolling and then welding it to form the stent, or coiling a zig-zag wire to form the stent, e.g. U.S. Pat. No. 6,136,023 to Boyle. In addition, hoops or rings may be cut from tubing stock, the tube elements stamped to form crowns, and the crowns connected by welding or laser fusion to form the stent, e.g. U.S. Pat. No. 5,817,152 to Birdsall.

In certain embodiments, a radiopaque material may include one or more of palladium (Pd), platinum (Pt), gold (Au), silver (Ag), iridium (Ir), nickel (Ni), titanium (Ti), copper (Cu), and zinc (Zn).

In certain embodiments, the radiopaque material includes metals such as palladium (Pd), platinum (Pt), gold (Au), silver (Ag), or combinations thereof. In certain embodiments, the radiopaque material includes one or more of these metals and optionally one or more of metals such as iridium (Ir), nickel (Ni), titantium (Ti), copper (Cu), zinc (Zn), or combinations thereof. The radiopaque material may be in elemental form or alloy form, for example.

In certain embodiments, the radiopaque material includes elemental palladium (Pd); elemental platinum (Pt); elemental gold (Au); elemental silver (Ag), and various alloys of one or more of these metals with each other and/or other metals. Exemplary alloys include an alloy of platinum (Pt) and iridium (Ir); an alloy of gold (Au), nickel (Ni), and titanium (Ti); an alloy of gold (Au), palladium (Pd), nickel (Ni), and titanium (Ti); an alloy of gold (Au), silver (Ag), copper (Cu), and Zinc (Zn) (e.g., 22 K yellow gold); an alloy of gold (Au) and platinum (Pt) or palladium (Pd) (e.g., 18 K white gold); an alloy of silver (Ag), palladium (Pd), and gold (Au); an alloy of silver (Ag) and platinum (Pt); an alloy of silver (Ag) and gold (Au); an alloy of nickel (Ni) and platinum (Pt).

In the context of alloys, herein, percentages are by mass.

Exemplary alloys of platinum and iridium include Pt-10Ir alloy (i.e., 90% platinum and 10% iridium) and Pt-20Ir alloy (i.e., 80% platinum and 20% iridium).

Exemplary alloys of gold (Au), nickel (Ni), and titanium (Ti) include Au—Ni—Ti alloy such as that described in U.S. Pat. No. 4,938,922, which includes the following composition, by weight: 91-99% gold, 0.5-7% nickel; 0.10-2% titanium.

Exemplary alloys of gold (Au), palladium (Pd), nickel (Ni), and titanium (Ti) include Au—Pd—Ni—Ti alloy such as that described in U.S. Pat. No. 4,938,922, which includes the following composition, by weight: 83-96% gold; 3-10% palladium; 0.5-5% nickel; and 0.10-2% titanium.

Exemplary alloys of gold (Au), silver (Ag), copper (Cu), and zinc (Zn) include one with the following composition, by weight: 91.67% gold; 5% silver; 2% copper; and 1.33% titanium.

Exemplary alloys of gold (Au), and platinum (Pt) or palladium (Pd) include those with the following compositions, by weight: 75% gold; and 25% platinum or palladium.

Exemplary alloys of gold (Au), and platinum (Pt) or palladium (Pd) include one with the following composition, by weight: 75% gold; and 25% platinum or palladium.

Exemplary alloys of silver (Ag) and gold (Au) include one with the following composition, by weight: 92.5% silver with a touch of gold. This is also called Karat sterling.

Exemplary alloys of silver (Ag) and platinum (Pt) include one with the following composition, by weight: 93.5% silver; and 6.5% platinum.

Exemplary alloys of silver (Ag), palladium (Pd), and gold (Au) include one with the following composition, by weight: 95% silver; 1% palladium; and 0.5% gold.

Exemplary alloys of nickel and platinum include Ni-33Pt alloy, which includes the following composition, by weight: 67% nickel; and 33% platinum.

In certain embodiments, the stent body includes (i.e., is made from) a CoNiCrMo alloy (cobalt-nickel-chromium-molybdenum alloy), a Ni—Cr alloy (nickel-chromium alloy), a low carbon stainless steel, or a Ni—Ti alloy (titanium-nickel alloy).

An exemplary CoNiCrMo alloy includes one with the following composition, by weight: 35% cobalt (Co); 35% nickel (Ni); 20% chromium (Cr); and 10% molybdenum (Mo). It is sold under the trademark MP35N.

An exemplary Ni—Cr alloy includes one with the following composition, by weight: minimum 58% nickel (Ni); 20.0-23.0% chromium (Cr); maximum 5% iron (Fe); and 8.0-10.0% molybdenum (Mo). It is sold under the tradename INCONEL 625.

An exemplary low carbon stainless steel is grade 316L, which comprises 16-18.5% chromium (Cr), 10-14% nickel (Ni), and 2-3% molybdenum (Mo).

Exemplary binary Ni—Ti alloys include, e.g., nitinol 55 and nitinol 60, which have roughly equal amounts of nickel (Ni) and titanium (Ti).

Figure 2:
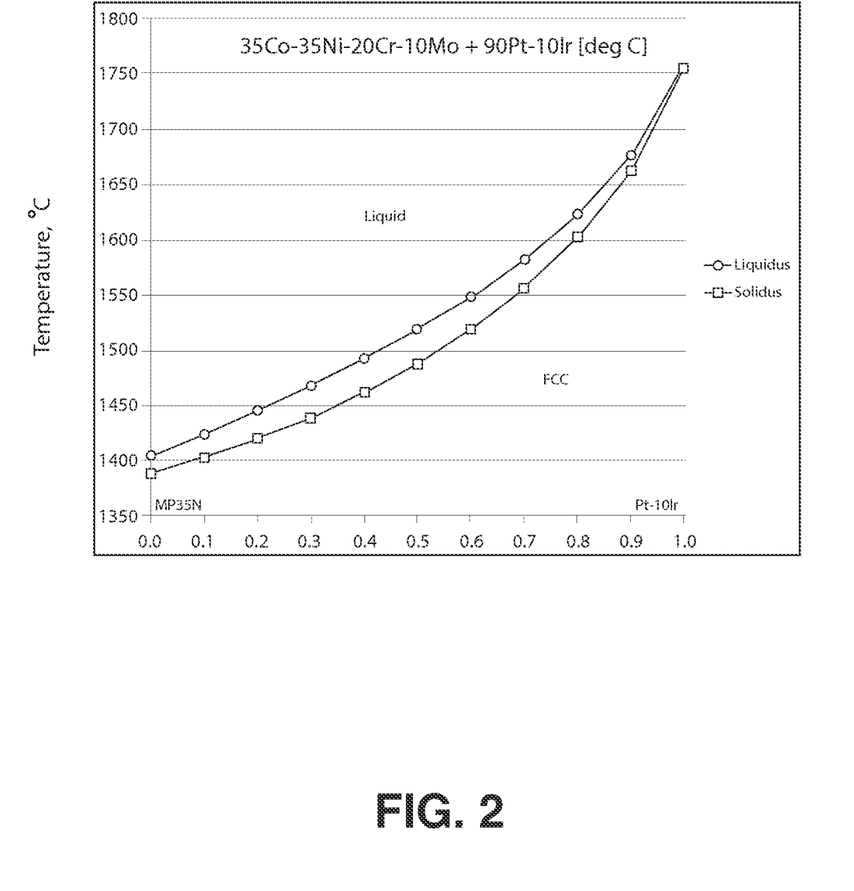
FIG. 2 shows the phase diagram of an exemplary MP35N—Pt10Ir system.

The selection of the material of the stent body (and the struts formed therein) and the radiopaque material depends on their solubilities with each other. That is, desirable materials are selected and matched such that only a single phase is formed under the conditions of forming the weld joint. For example, FIG. 2 shows the phase diagram for matrix face-centered-cubic phase of MP35N and Pt10Ir. The diagram shows the two components to be sufficiently soluble in each other at high temperatures. At low temperatures, interaction between certain components such as Co—Pt, Ni—Pt, Cr—Pt, etc. shows second phase precipitation. Because the processes that involve laser result in rapid solidification of meltpool, hence the precipitation of second phases is minimized. Presence of significant amounts of second phase in weld joint is undesirable because it can cause brittleness of the weld joint.

For certain material combinations, there may be a solubility (i.e., miscibility) gap under the conditions of forming a weld joint, and phase separation may occur. For example, gold and nickel form two immiscible phases of FCC Au and FCC Ni at 726° C., but the phase separation is not generally detrimental to weld mechanical properties.

In certain embodiments, the stent body includes a CoNiCrMo alloy such as MP35N, and the radiopaque material includes elemental Pt; a Pt—Ir alloy such as Pt-10Ir alloy or Pt-20Ir alloy; elemental Pd; a Ni—Pt alloy such as Ni-33Pt alloy; elemental Au; elemental Ag; a Au—Pt alloy; a Au—Pd alloy; a Au—Ag—Cu—Zn alloy; elemental Ag; a Ag—Pd—Au alloy; a Ag—Au alloy; or a Ag—Pt alloy.

In certain embodiments, the stent body includes a Ni—Cr alloy such as INCONEL 625, and the radiopaque material includes elemental Pt; a Pt—Ir alloy such as Pt-10Ir alloy and Pt-20Ir alloy; elemental Pd; a Ni—Pt alloy such as Ni-33Pt alloy; elemental Au; elemental Ag; a Au—Pt alloy; a Au—Pd alloy; a Au—Ag—Cu—Zn alloy; elemental Ag; a Ag—Pd—Au alloy; a Ag—Au alloy; a Ag—Pt alloy; a Au—Ni—Ti alloy; or a Au—Pd—Ni—Ti alloy.

In certain embodiments, the stent body includes a low carbon stainless steel, and the radiopaque material includes a Ni—Pt alloy such as Ni-33Pt alloy; elemental Au; a Au—Ni—Ti alloy; a Au—Pd—Ni—Ti alloy; a Au—Pt alloy; a Au—Pd alloy; a Au—Ag—Cu—Zn alloy; elemental Ag; a Ag—Pd—Au alloy; a Ag—Au alloy; or a Ag—Pt alloy.

In certain embodiments, the stent body includes a Ni—Ti alloy, and the radiopaque material includes elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, or a Ag—Pt alloy.

In certain embodiments, the weld joint has a tensile strength similar to that of the stent body portions being joined. In certain embodiments, the one or more welds possess a strength of 1-2 pounds break load.

For certain radiopaque materials, more welds may be necessary to provide the overall mechanical properties desired. For example, gold welds may be more ductile and hence the stent will have to accommodate the loss in radial strength by adding more welds.

Stent constructions of the present disclosure are made by a method that includes using a radiopaque filler material in a welding process (e.g., laser welding, spot welding, resistance welding, MIG welding). More specifically, a method of the present disclosure provides a method of making a stent that includes: providing a stent having a stent body with one or more struts constructed of stent body material; providing a radiopaque filler material that is different from the stent body material; and welding the stent body at a junction between the one or more struts with the radiopaque filler material to form one or more weld joints comprising the radiopaque material. The welding process forms a molten mixture of the radiopaque filler material and material that forms the stent body, which then forms a solid mixture, thereby defining a weld joint.

In certain embodiments, the radiopaque filler material is provided in the form of a radiopaque filler wire. In certain embodiments, the radiopaque filler wire has a diameter of at least 0.002 inch. In certain embodiments, the radiopaque filler wire has a diameter of no greater than the diameter or thickness of the stent crown portions of the struts.

In certain embodiments, the welding occurs using a laser of sufficient power to melt the stent body material and/or the radiopaque filler material. In certain embodiments, the laser is a 50-100 Watt YAG laser. The choice of welding system can be readily determined by one of skill in the art.

Also, the conditions for forming the weld joints can be readily determined by one of skill in the art. Typically, the power chosen is that sufficient to melt the stent body material and/or the radiopaque material (in certain embodiments, the radiopaque material, and in certain embodiments, both) and form a meltpool. In the case of platinum, a relatively high power is needed, and the material of the adjacent weldable crowns of the stent body may also melt; however, if platinum is soluble in some of the resultant alloys formed upon mixing in the meltpool, a strong weld joint may still form. For example, for a platinum wire, 3.7 ms pulse length, 40 microns aperture, and a power setting of 2.9 KV may be used.

In the case of gold, the melting point is lower than that of platinum, so a lower power should be sufficient to create a meltpool and wet the surfaces of the weldable crowns and not initiate any un-wanted formation of chemical compounds.

Figure 3:
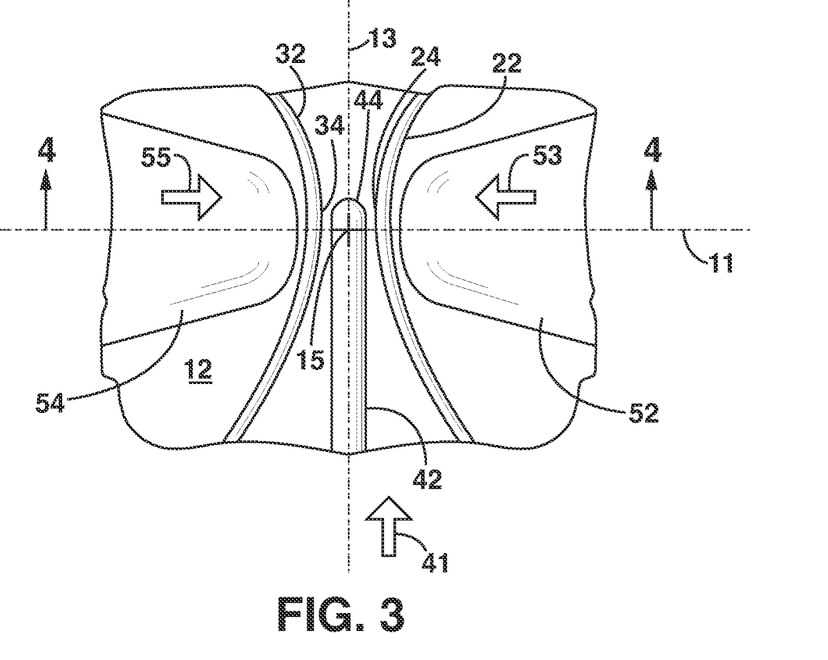
FIG. 3 depicts a portion of one exemplary apparatus that may be used to form weld joints in stents as described herein.
Figure 4:
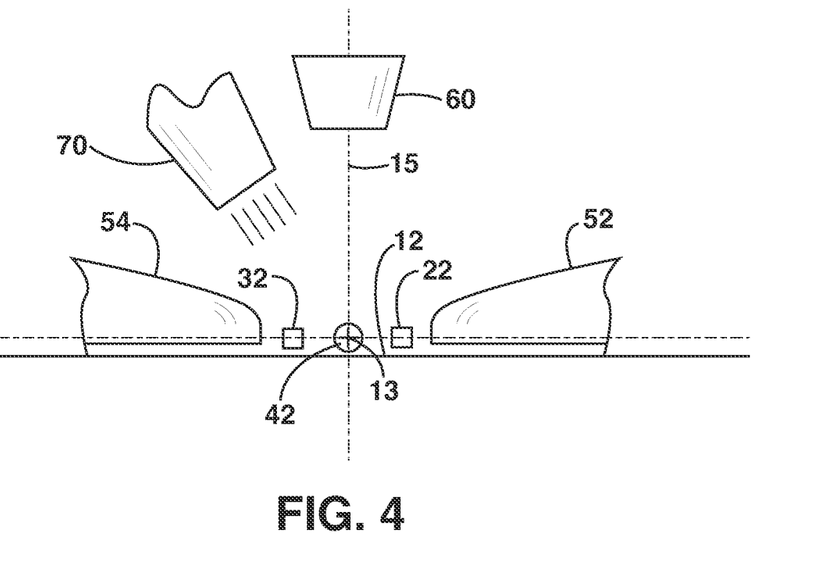
FIG. 4 is a cross-sectional view of the apparatus of FIG. 3 taken along line 4-4 in FIG. 3.

One exemplary apparatus that may be used to form weld joints in stents as described herein is depicted in FIGS. 3 and 4. As depicted in FIGS. 3 and 4, the exemplary apparatus is configured to form a weld joint between adjacent crown portions 24 and 34 in adjacent struts 22 and 32. In the view depicted in FIG. 3, the weld joint 40 (see, e.g., FIG. 1A) is not yet formed. The exemplary apparatus depicted in FIGS. 3 and 4 includes fixturing configured to move and hold the struts 22 and 32 and filler wire 42 in position on a fixture surface 12 to form the weld joint.

In particular, the exemplary apparatus includes feet 52 and 54 that are moved towards each other over surface 12 along axis 11 in the direction of arrows 53 and 55. In one or more embodiments, both feet 52 and 54 may be moved in the direction of their respective arrows 53 and 55. In one or more alternative embodiments, only one of the feet 52 or 54 is moved along axis 11 while the other foot remains in a fixed or stationary position.

Moving the feet 52 and 54 towards each other along axis 11 causes, in one or more embodiments, the struts 22 and 32 to be moved towards each other between the feet 52 and 54. In the depicted exemplary embodiment, the feet 52 and 54 may be shaped and positioned to move the crowns 24 and 34 of the struts 22 and 32 towards each other. The feet 52 and 54 may be moved as described herein by any suitable drive mechanism such as, e.g., electric motors, hydraulics, magnetic drive systems, etc.

In addition to feet 52 and 54, the exemplary apparatus includes a filler wire feed mechanism capable of moving filler wire 42 into position to form the weld joints described herein. As seen in, e.g., FIG. 3, the filler wire 42 may, in one or more embodiments, be advanced into position between struts 22 and 32 in the direction of arrow 41 along axis 13. In one or more embodiments, the distal or free end 44 of filler wire 42 may be positioned at or near the location where weld joint 40 is to be formed between struts 22 and 32.

With the struts 22 and 32 and filler wire 42 in position, weld energy is directed along axis 15 at the junction between the struts 22 and 32 to form weld joint 40. With reference to FIG. 4, the exemplary apparatus includes a laser 60 configured to deliver weld energy in the form of laser light to form the weld joints described herein. In one or more embodiments, the exemplary apparatus may include an optional gas source 70 configured to direct one or more inert gases at the weld joint during formation to limit the production of unwanted compositions in the weld joint (e.g., oxides, etc.). Alternative apparatus may use other forms of weld energy to form the weld joints, e.g., ultrasonic energy, electrical resistance heating, etc.

ILLUSTRATIVE EMBODIMENTS

Embodiment 1 is a stent comprising a stent body and one or more weld joints, wherein a radiopaque material (which, in certain embodiments, may include one or more of Pd, Pt, Au, Ag, Ir, Ni, Ti, Cu, Zn) is localized at the weld joints.

Embodiment 2 is the stent of embodiment 1 wherein the radiopaque material comprises (or consists essentially of, or consists of) Pd, Pt, Au, Ag, or combinations thereof (with each other or with other metals).

Embodiment 3 is the stent of embodiment 2 wherein the radiopaque material further comprises (or consists essentially of, or consists of) Ir, Ni, Ti, Cu, Zn, or combinations thereof.

Embodiment 4 is the stent of embodiment 2 wherein the radiopaque material comprises (or consists essentially of, or consists of) elemental Pt, elemental Pd, a Pt—Ir alloy, elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, a Ag—Pt alloy, or a Ni—Pt alloy.

Embodiment 5 is the stent of any one of embodiments 1 through 4 wherein the stent body comprises (or consists essentially or, or consists of) a CoNiCrMo alloy, a Ni—Cr alloy, a low carbon stainless steel, or a Ni—Ti alloy.

Embodiment 6 is the stent of embodiment 5 wherein the material of the stent comprises (or consists essentially of, or consists of) a CoNiCrMo alloy.

Embodiment 7 is the stent of embodiment 6 wherein the radiopaque material comprises (or consists essentially of, or consists of) elemental Pt, a Pt—Ir alloy, elemental Pd, a Ni—Pt alloy, elemental Au, elemental Ag, a Au—Pt alloy, a Au—Pd alloy, a Au—Ag—Cu—Zn alloy, a Ag—Pd—Au alloy, a Ag—Au alloy, or a Ag—Pt alloy.

Embodiment 8 is the stent of embodiment 5 wherein the material of the stent comprises (or consists essentially of, or consists of) a Ni—Cr alloy.

Embodiment 9 is the stent of embodiment 8 wherein the radiopaque material comprises (or consists essentially of, or consists of) elemental Pt, a Pt—Ir alloy, elemental Pd, a Ni—Pt alloy, elemental Au, elemental Ag, a Au—Pt alloy, a Au—Pd alloy, a Au—Ag—Cu—Zn alloy, elemental Ag, a Ag—Pd—Au alloy, a Ag—Au alloy, a Ag—Pt alloy, a Au—Ni—Ti alloy, or a Au—Pd—Ni—Ti alloy.

Embodiment 10 is the stent of embodiment 5 wherein the material of the stent comprises (or consists essentially of, or consists of) a low carbon stainless steel.

Embodiment 11 is the stent of embodiment 10 wherein the radiopaque material comprises (or consists essentially of, or consists of) a Ni—Pt alloy, elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, or a Ag—Pt alloy.

Embodiment 12 is the stent of embodiment 5 wherein the material of the stent comprises (or consists essentially of, or consists of) a Ni—Ti alloy.

Embodiment 13 is the stent of embodiment 12 wherein the radiopaque material comprises (or consists essentially of, or consists of) elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, or a Ag—Pt alloy.

Embodiment 14 is the stent of any of embodiments 1 through 13 wherein the one or more weld joints possess a tensile strength of 1-2 pounds break load.

Embodiment 15 is a stent comprising a stent body and one or more weld joints, wherein the weld joints comprise a radiopaque material selected from the group of elemental Pt, a Pt-10Ir alloy, a Pt-20Ir alloy, elemental Pd, a Ni-33Pt alloy, elemental Au, elemental Ag, a Au—Pt alloy, a Au—Pd alloy, a Au—Ag—Cu—Zn alloy, a Ag—Pd—Au alloy, a Ag—Au alloy, a Ag—Pt alloy, a Au—Ni—Ti alloy, or a Au—Pd—Ni—Ti alloy.

Embodiment 16 is a method of making a stent, the method comprising (or consisting essentially of, or consisting of):
providing a stent having a stent body with one or struts constructed of stent body material;
providing a radiopaque filler material that is different from the stent body material; and
welding the stent body at a junction between the one or more struts with the radiopaque filler material to form one or more weld joints comprising the radiopaque material.

Embodiment 17 is the method of embodiment 16 wherein the radiopaque material comprises (or consists essentially of, or consists of) Pd, Pt, Au, Ag, or combinations thereof (with each other or with other metals).

Embodiment 18 is the method of embodiment 17 wherein the radiopaque material further comprises (or consists essentially of, or consists of) Ir, Ni, Ti, Cu, Zn, or combinations thereof.

Embodiment 19 is the method of embodiment 17 wherein the radiopaque material comprises (or consists essentially of, or consists of)
elemental Pt, elemental Pd, a Pt—Ir alloy, elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, a Ag—Pt alloy, or a Ni—Pt alloy.

Embodiment 20 is the method of embodiment 16 wherein the stent body comprises (or consists essentially of, or consists of) a CoNiCrMo alloy, a NiCr alloy, a low carbon stainless steel, or a Ni—Ti alloy.

Embodiment 21 is the method of any of embodiments 16 through 20 wherein the radiopaque filler material comprises a radiopaque filler wire.

Embodiment 22 is the method of embodiment 21 wherein the radiopaque filler wire has a diameter of at least 0.002 inch.

Embodiment 23 is the method of embodiment 21 or 22 wherein the radiopaque filler wire has a diameter of no greater than the diameter or thickness of the stent struts (particularly at the crown portions of the struts).

Embodiment 24 is the method of any of embodiments 16 through 23 wherein the one or more weld joints possess a tensile strength of 1-2 pounds break load.

Embodiment 25 is the method of any of embodiments 16 through 24 wherein the welding occurs using a laser of sufficient power to melt the stent body material and/or radiopaque filler material.

All patents, patent documents, and references cited herein are incorporated in their entirety as if each were incorporated separately. This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the exemplary apparatus described herein. Various modifications of the illustrative embodiments, as well as additional embodiments of the disclosure, will be apparent upon reference to this description.

What is claimed:
1. A stent comprising:
a stent body having struts of a weldable stent body material;
one or more weld joints connecting the struts; and
a radiopaque filler material different from the material of the stent body and being localized at the weld joints;
wherein the stent body material and the filler material are mutually soluble and are combined in the weld joints in only a single phase;
wherein the weld joints have a tensile strength of 1-2 pounds break load such that the stent has sufficient radial strength to support the walls of a vessel lumen and maintain the lumen in an open state.
2. The stent of claim 1 wherein the radiopaque filler material comprises Pd, Pt, Au, Ag, or combinations thereof.
3. The stent of claim 2 wherein the radiopaque filler material further comprises Ir, Ni, Ti, Cu, Zn, or combinations thereof.

4. The stent of claim 2 wherein the radiopaque filler material comprises elemental Pt, elemental Pd, a Pt—Ir alloy, elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, a Ag—Pt alloy, or a Ni—Pt alloy.

5. The stent of claim 1 wherein the stent body comprises a CoNiCrMo alloy, a Ni—Cr alloy, a low carbon stainless steel, or a Ni—Ti alloy.

6. The stent of claim 5 wherein the stent body material comprises a CoNiCrMo alloy.

7. The stent of claim 6 wherein the radiopaque filler material comprises elemental Pt, a Pt—Ir alloy, elemental Pd, a Ni—Pt alloy, elemental Au, elemental Ag, a Au—Pt alloy, a Au—Pd alloy, a Au—Ag—Cu—Zn alloy, a Ag—Pd—Au alloy, a Ag—Au alloy, or a Ag—Pt alloy.

8. The stent of claim 5 wherein the stent body material comprises a Ni—Cr alloy.

9. The stent of claim 8 wherein the radiopaque filler material comprises elemental Pt, a Pt—Ir alloy, elemental Pd, a Ni—Pt alloy, elemental Au, elemental Ag, a Au—Pt alloy, a Au—Pd alloy, a Au—Ag—Cu—Zn alloy, elemental Ag, a Ag—Pd—Au alloy, a Ag—Au alloy, a Ag—Pt alloy, a Au—Ni—Ti alloy, or a Au—Pd—Ni—Ti alloy.

10. The stent of claim 5 wherein the stent body material comprises a low carbon stainless steel.

11. The stent of claim 10 wherein the radiopaque filler material comprises a Ni—Pt alloy, elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, or a Ag—Pt alloy.

12. The stent of claim 5 wherein the stent body material comprises a Ni—Ti alloy.

13. The stent of claim 12 wherein the radiopaque filler material comprises elemental Au, a Au—Ni—Ti alloy, a Au—Pd—Ni—Ti alloy, a Au—Pt alloy, a Au—Pd alloy, a Au—Ag—Cu—Zn alloy, elemental Ag, a Ag—Pd—Au alloy, a Ag—Au alloy, or a Ag—Pt alloy.

14. A stent comprising a stent body material and one or more weld joints:
   wherein the weld joints comprise a radiopaque material selected from the group of elemental Pt, a Pt-10Ir alloy, a Pt-20Ir alloy, elemental Pd, a Ni-33Pt alloy, elemental Au, elemental Ag, a Au—Pt alloy, a Au—Pd alloy, a Au—Ag—Cu—Zn alloy, a Ag—Pd—Au alloy, a Ag—Au alloy, a Ag—Pt alloy, a Au—Ni—Ti alloy, or a Au—Pd—Ni—Ti alloy; and
   wherein the stent body material and the radiopaque material are different and mutually soluble and are combined in the weld joints in only a single phase;
   wherein the weld joints have a tensile strength of 1-2 pounds break load such that the stent has sufficient radial strength to support the walls of a vessel lumen and maintain the lumen in an open state.

15. A method of making a stent, the method comprising;
   providing a stent body with one or more struts constructed of weldable stent body material;
   providing a radiopaque filler material that is different from the stent body material; and
   welding the stent body at a junction between the one or more struts with the radiopaque filler material to form one or more weld joints comprising the radiopaque material;
   wherein the stent body material and the filler material are mutually soluble and are combined in the weld joints in only a single phase;
   wherein the weld joints have a tensile strength of 1-2 pounds break load such that the stent has sufficient radial strength to support the walls of a vessel lumen and maintain the lumen in an open state.

16. The method of claim 15 wherein the radiopaque filler material comprises Pd, Pt, Au, Ag, or combinations thereof.

17. The method of claim 16 wherein the radiopaque filler material further comprises Ir, Ni, Ti, Cu, Zn, or combinations thereof.

18. The method of claim 16 wherein the radiopaque filler material comprises elemental Pt, elemental Pd, a Pt—Ir alloy, elemental Au, a Au—Ni—Ti alloy, a Au—Pd—Ni—Ti alloy, a Au—Pt alloy, a Au—Pd alloy, a Au—Ag—Cu-Zn alloy, elemental Ag, a Ag—Pd—Au alloy, a Ag—Au alloy, a Ag—Pt alloy, or a Ni—Pt alloy.

19. The method of claim 15 wherein the stent body comprises a CoNiCrMo alloy, a Ni—Cr alloy, a low carbon stainless steel, or a Ni—Ti alloy.

20. The method of claim 15 wherein the radiopaque filler material comprises a radiopaque filler wire.

21. The method of claim 20 wherein the radiopaque filler wire has a diameter of at least 0.002 inch.

22. The method of claim 20 wherein the radiopaque filler wire has a diameter of no greater than the diameter of the stent at the struts.

23. The method of claim 15 wherein the welding occurs using a laser of sufficient power to melt the stent body material and the radiopaque filler material.

* * * * *